United States Patent [19]

Force et al.

[11] 3,953,479
[45] Apr. 27, 1976

[54] DIGLYCIDYL ESTERS OF $C_{21}$-CYCLOALIPHATIC DICARBOXYLIC ACID

[75] Inventors: Carlton G. Force, Mount Pleasant; Benjamin F. Ward, Isle of Palms, both of S.C.

[73] Assignee: Westvaco Corporation, New York, N.Y.

[22] Filed: Feb. 3, 1975

[21] Appl. No.: 546,505

Related U.S. Application Data

[63] Continuation-in-part of Ser. No. 393,959, Sept. 4, 1973, abandoned.

[52] U.S. Cl............................................ 260/348 A
[51] Int. Cl.²...................................... C07D 303/44
[58] Field of Search................................ 260/348 A

[56] References Cited
UNITED STATES PATENTS

| | | | |
|---|---|---|---|
| 2,895,947 | 7/1959 | Shokal et al. | 260/348 A |
| 3,075,999 | 1/1963 | June et al. | 260/348 A |
| 3,651,098 | 3/1972 | Heer et al. | 260/348 A |
| 3,816,365 | 6/1974 | Schmid et al. | 260/348 A |

FOREIGN PATENTS OR APPLICATIONS 1,032,363   6/1966   United Kingdom

OTHER PUBLICATIONS
Chemical Abstracts, Vol. 53, p. 1831e.

*Primary Examiner*—Norma S. Milestone
*Attorney, Agent, or Firm*—Richard L. Schmalz; Ernest B. Lipscomb, III

[57] ABSTRACT

There is provided by way of this invention diglycidyl esters of $C_{21}$-dicarboxylic acid represented by the structural formula

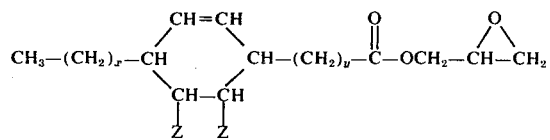

wherein $x$ and $y$ are integers from 3 to 9, $x$ and $y$ together equal 12, and Z is a member of the group consisting essentially of

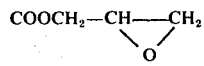

and hydrogen with one Z of each moiety.

1 Claim, No Drawings

DIGLYCIDYL ESTERS OF $C_{21}$-CYCLOALIPHATIC DICARBOXYLIC ACID

CROSS-REFERENCE TO RELATED APPLICATION

This application is a continuation-in-part of copending application Ser. No. 393,959 filed Sept. 4, 1973 and now abandoned.

BACKGROUND OF THE INVENTION

1. Field of the Invention

This invention relates to new compounds from a $C_{21}$-cycloaliphatic dicarboxylic acid. More particularly, this invention relates to diglycidyl esters of $C_{21}$-cycloaliphatic dicarboxylic acids and how to make them.

2. The Prior Art

It is known that glycidyl esters of dimer and trimer fatty acids have been used as acid scavengers in synthetic ester lubricants, as chemical intermediates for making polyepoxide films, in adhesives, and as components in moulding materials, among others.

Glycidyl esters of dimer and trimer fatty acids, have been prepared by first preparing the alkali metal salt of the acid in the presence of a solvent, dehydrating this salt and then reacting the salt with an epoxy halo-substituted compound having a 1,2-epoxy group, such as epichlorohydrin, in the presence of a suitable catalyst. Unfortunately, preparation of the intermediate salt of the dimer ester is slow and unduly difficult because of foaming phenomenon during water evolution. Moreover, caking and stirring complications due to the high viscosity of the soap gel, slow filtration rates and removing any unreacted soap gel from the reaction product further render this method altogether undesirable. Improvements in the prior art for making the diglycidyl ester of dimer acids have been made, such as in U.S. Pat. No. 3,075,999 to June et al. wherein an ester having a viscosity above 400 centipoise at 25°C. was produced.

It has been found that a low viscosity, i.e., below 400 centipoise at 25°C. diglycidyl ester of a $C_{21}$-cycloaliphatic dicarboxylic acid may be made. It is, therefore, the general object of this invention to provide new diglycidyl ester compounds.

Another object of this invention is to provide a diglycidyl ester of a $C_{21}$-cycloaliphatic dicarboxylic acid having a low viscosity.

A further object of this invention is to provide a process for making these ester compounds from $C_{21}$-cycloaliphatic dicarboxylic acid salts that are fluid at near anhydrous salt concentrations and that easily react.

Further objects, features and advantages of this invention will become evident from the foregoing detailed description of the invention.

DETAILED DESCRIPTION OF THE INVENTION

This invention provides diglycidyl esters of $C_{21}$-dicarboxylic acid represented by the structural formula

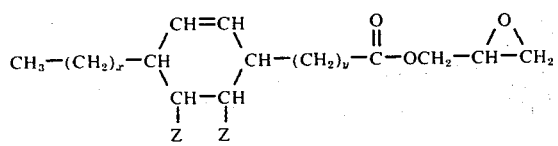

wherein $x$ and $y$ are integers from 3 to 9, $x$ and $y$ together equal 12, and Z is a member of the group consisting essentially of hydrogen and

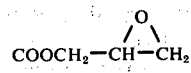

with one Z of each moiety.

The $C_{21}$-cycloaliphatic dicarboxylic acid salt is the fatty acid starting material. The potassium salt of the $C_{21}$-cycloaliphatic dicarboxylic acid is the preferred of the alkali metal salts, but salts of other cations may also be used, such as sodium, lithium, calcium or ammonium. These salts are more fully set forth in U.S. Pat. No. 3,734,859, which issued May 22, 1973, and is incorporated herein by reference.

When a mixture of an alkali metal salt of predominately 5-carboxy-4-hexyl-2 cyclohexene-1-octanoic acid and 6-carboxy-4 hexyl-2 cyclohexene-1-octanoic acid is made into the diglycidyl ester, the isomer mixture formed provides not only the advantages of a conventional ester, but also provides additional advantages such as, in particular, a wider temperature range of application and no gel formation. The mixture of the acids of these two isomers is represented by the structural formula

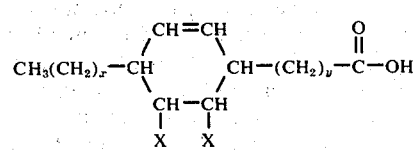

wherein $x$ and $y$ are integers from 3 to 9, $x$ and $y$ together equal 12, where X is a member of the group consisting of hydrogen and COOH, with one X of each moiety. Although the isomers wherein $x$ is 5 and $y$ is 7 form a preponderance of the composition, there are minor amounts of the $C_{21}$-dicarboxylic acid where the cyclohexene ring varies in position along the carbon chain. For the purpose of this specification, compositions of the general formulation shown above are termed "$C_{21}$-dicarboxylic acids".

The $C_{21}$-dicarboxylic acids used in this invention are produced from linoleic acid of various animal, vegetable and tall oil sources. The $C_{21}$-dicarboxylic acids may be made by reacting linoleic acid with acrylic acid and catalytic amounts of iodine. One such process for making the $C_{21}$-dicarboxylic acids for use in the esters of this invention is set forth in U.S. Pat. No. 3,753,968 which issued Aug. 21, 1973.

The diglycidyl ester is made by reacting the $C_{21}$-dicarboxylic acid salt with epichlorohydrin. The equivalent ratios of the epichlorohydrin to $C_{21}$-dicarboxylic acid salt may vary considerably without departing from the scope of the invention. For example, the equivalent ratio of epichlorophydrin to $C_{21}$-dicarboxylic acid salt may range from 15:1 to 2:1. The reaction is preferably carried out at a ratio of epichlorohydrin to $C_{21}$-dicarboxylic acid of 10:1.

One method of making the diglycidyl esters is to react the $C_{21}$-dicarboxylic acid with epichlorohydrin in the presence of caustic. The diester is formed by refluxing the $C_{21}$-dicarboxylic acid, caustic to form the salt, and the epichlorohydrin together at a temperature between 70°C. and 140°C., preferably 95°C. to 117°C., with stirring. The reaction is conducted for ½ – 4 hours to obtain maximum reaction. The resulting product may then be purified by washing and distilling. The time required for the addition of the alkali may also vary considerably. However, it is preferred that the alkali be metered into the reaction vessel at a controlled rate. An addition rate over about 1 hour is most preferred. The initial reaction, as indicated, may be carried on at 117°C. Experiments have shown that, if desired, temperatures about 117°C. and below 95°C. may be employed. The reaction may be carried out at a temperature of 95°C. to 117°C. at atmospheric pressure or above, and below this range under vacuum or pressure. Excessively high temperatures have been found to degrade the product. It is preferable to employ the $C_{21}$-dicarboxylic acid salt in a substantially anhydrous condition as it is very fluid at 100°C. and therefore mixes and reacts readily with the epichlorohydrin.

Alkaline materials which may be employed for the purposes of the present invention are potassium hydroxide, sodium hydroxide, lithium hydroxide, calcium hydroxide and magnesium hydroxide, as well as, magnesium oxide, calcium oxide and ammonia. The potassium hydroxide and sodium hydroxide are preferred and may be added in the form of pellets or in solution. It will be readily understood, however, that the invention is not restricted to these specific alkaline materials but that the invention encompasses the employment of any alkaline material when added to epichlorohydrin, containing the $C_{21}$-dicarboxylic acid and catalyst.

Using the process outlined above, the diglycidyl ester reaction may be accomplished without the aid of a catalyst. However, it may be desirable to employ a tertiary amine catalyst or quaternary salt catalyst. The amount of the tertiary amine or quaternary salt to be used in the process may vary over a considerable range. Generally, the amine or salt will be employed in amounts varying from about 0.01% to 5% by weight of the $C_{21}$-dicarboxylic acid salt. Preferred amounts vary from about .01% to 3% by weight of the salt.

The quaternary salts that may be used as catalysts for the reaction are those of the formula

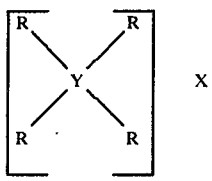

wherein Y is nitrogen, phosphorous or arsenic, X is an ion of an inorganic acid, and R is a hydrocarbon radical, such as an alkyl, cycloalkyl, aryl, alkaryl arylalkyl, and the like, radicals. Preferably Y is nitrogen, R is an alkyl, aryl or arylalkyl radical, preferably containing no more than 12 carbons and X is a chlorine or bromine, such as benzyltrimethylammonium chloride, benzyltrimethylammonium bromide, phenyltrioctylammonium chloride, tetrabutylammonium chloride and tetraoctylammonium chloride. Tetraethylammonium bromide is the most preferred quaternary salt catalyst for the purpose of the present invention. Examples of other salts include, among others, phenyltributylammonium chloride, cyclohexyltributylammonium sulfate, benzyltrimethylammonium sulfate, benzyltrimethylphosphonium chloride, phenyltrioctylammonium sulfate, phenyltriethylarsonium chloride, tetramethylammonium chloride, tetrabutylammonium sulfate, tetraoctylammonium nitrate, diphenyldimethylammonium borate, diphenyldioctylammonium chloride, benzyltrimethylammonium borate, diphenyldimethylphosphonium chloride, dicyclohexyldiethylarsonium chloride, benzyltrinonylammonium chloride, and benzyltridodecylammonium sulfate.

The tertiary amines that may be used as catalysts are those mono- or poly-amines having an open chain or cyclic structure which have all the amine hydrogen replaced by suitable substituents, such as hydrocarbon radicals, and preferably aliphatic, cycloaliphatic, or aromatic radicals. Examples of these amines include, among others, triethylamine, tributylamine, dimethyl benzylamine, tricyclohexylamine, pyridine, quinoline, and the like. Preferred amines are the trialkyl, tricycloalkyl and triaryl amines, such as triethylamines, triphenyl amine, tri-(2,3-dimethylcyclohexyl) amine, and the like.

Highest product quality was found at about 110°C., a ratio of 10:1 of epichlorohydrin to $C_{21}$-dicarboxylic acid and a 35-minute addition time. An ester made under these conditions from 50% $C_{21}$-cycloaliphatic dicarboxylic acid contained 0.26 equivalent per 100 per grams epoxide (91% of theory) and only 0.25% by weight of chlorine.

The advantage of the diglycidyl esters of the subject invention include, among other things, a low weight per epoxide (referred to herein as W.P.E.) and low viscosity as compared to diglycidyl esters made from dimer acids. For example, the theoretical W.P.E. of the diglycidyl esters of the subject invention is 232 and pilot plant cooks have been obtained as low as 247. Typical W.P.E.'s for dimer diglycidyl esters are above 400. The low viscosity of the diglycidyl esters is another important advantage. A viscosity even without catalyst of 445 centipoise has been obtained; whereas, with catalyst viscosities of below 400 centipoise at 25°C. are typical.

These advantages of the diglycidyl ester of the $C_{21}$-dicarboxylic acid make them replacements for the diglycidyl diesters of dimer acids in many uses and in some uses superior to the dimers glycidyl esters. For example, diglycidyl esters of the $C_{21}$-dicarboxylic acid in resin formulations are especially advantageous because of there low viscosity.

Other applications include in U.V. curing ink formulations, in adhesives and in lubricants.

The process of the present invention is best illustrated by the following specific examples.

EXAMPLE 1

A diglycidyl diester from a $C_{21}$-cycloaliphatic dicarboxylic acid and epichlorohydrin was made. 250 grams of $C_{21}$-dicarboxylic acid and 1,300 grams of epichlorohydrin were placed in a flask. To this was added 180 grams of 50% potassium hydroxide dropwise through a funnel to convert the acid to its salt form while refluxing at approximately 117°C. with stirring. The addition of the potassium hydroxide was adjusted to control the refluxing kettle temperature at 110°C. plus or minus 1°C. The water phase was continuously separated and withdrawn from the reflux. When addition of the potassium hydroxide was completed, the temperture was brought to 117°C. by continuous water separation overhead. No catalyst was added. The reaction was carried on for 35 minutes. Most of the water was taken off during the course of the reaction itself. The reaction mixture was then cooled to room temperature and the salt separated by filtration. The product yield was 80% based on acid. The W.P.E. was 410 and the viscosity was 445 centipoise at 25°C.

EXAMPLE 2

57.2 Pounds of the $C_{21}$-dicarboxylic acid was dissolved in 297.4 pounds of epichlorohydrin in a 50-gallon reactor equipped with a take-off condenser. A tetraethylammonium bromide catalyst (108 grams) was added to the mix. This solution was heated to about 110°C. and then 41 pounds of 50% KOH was added over a 90-minute period; the temperature being carefully controlled at 110°C. As the potassium hydroxide is added, the acid converts to its salt and then reacts with the epichlorohydrin. As soon as all the caustic had been added, the temperature was allowed to move up to 117°C. This is the boiling point of pure epichlorohydrin and thus indicates that all water has been azeotroped out of the reaction vessel. The diglycidyl ester formation was complete at this point so the mixture was filtered at room temperature to remove the potassium chloride and the polymer. The remainder of the epichlorohydrin was then removed by vacuum distillation at 55°C. The resulting product was the diglycidyl ester of $C_{21}$-dicarboxylic acid having a W.P.E. of 272 and a viscosity of 205 centipoise at 25°C.

EXAMPLE 3

This example compares the diglycidyl esters of the $C_{21}$-dicarboxylic acid (from Example 2) to a prior art diglycidyl ester made by the reaction of a dimer of linoleic acid and epichlorohydrin.

|  | Viscosity, Cps. at 25°C. | Epoxide Equivalent | Color Gardner |
|---|---|---|---|
| Invention (from Example 2) | 225 | 294 | 7 + |
| Glycidyl Ester of Dimer | 1,300 | 550 | 7½ |

While the invention has been described and illustrated herein by reference to various specific materials, procedures and examples, it is understood that the invention is not restricted to the particular materials, combinations of materials, and procedures selected for that purpose. Numerous variations of such details can be employed, as will be appreciated by those skilled in the art.

What is claimed is:

1. A compound having the structural formula

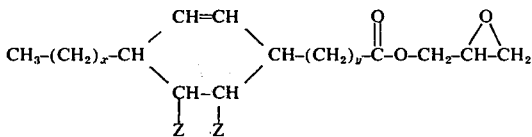

wherein $x$ and $y$ are integers from 3 to 9, $x$ and $y$ together equal 12, and Z is a member of the group consisting essentially of

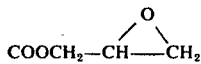

and hydrogen with one Z of each moiety.

* * * * *